United States Patent
Lesch, Jr.

(10) Patent No.: US 7,488,308 B2
(45) Date of Patent: Feb. 10, 2009

(54) INJECTOR WITH BYPASS CHANNEL

(75) Inventor: Paul R. Lesch, Jr., Lino Lakes, MN (US)

(73) Assignee: Antares Pharma, Inc., Minneapolis, MN (US)

( * ) Notice: Subject to any disclaimer, the term of this patent is extended or adjusted under 35 U.S.C. 154(b) by 0 days.

(21) Appl. No.: 10/917,419

(22) Filed: Aug. 13, 2004

(65) Prior Publication Data

US 2005/0020984 A1  Jan. 27, 2005

Related U.S. Application Data (63) Continuation of application No. PCT/US03/04382, filed on Feb. 14, 2003.

(60) Provisional application No. 60/357,236, filed on Feb. 15, 2002.

(51) Int. Cl.
*A61M 5/00* (2006.01)

(52) U.S. Cl. .................. 604/236; 604/187; 604/238; 604/249

(58) Field of Classification Search ......... 604/235–238, 604/268, 110, 187
See application file for complete search history.

(56) References Cited

U.S. PATENT DOCUMENTS

| | | | |
|---|---|---|---|
| 2,645,223 A | 7/1953 | Lawshe et al. | |
| 2,699,166 A | 1/1955 | Dickinson, Jr. et al. | |
| 2,728,341 A | 12/1955 | Roehr | |
| 2,893,390 A * | 7/1959 | Lockhart et al. | 604/238 |
| 3,375,825 A | 4/1968 | Keller | |
| 3,382,865 A | 5/1968 | Worrall, Jr. | |
| 3,526,225 A * | 9/1970 | Masahide | 604/71 |
| 3,557,784 A | 1/1971 | Shields | |
| 3,811,441 A | 5/1974 | Sarnoff | |
| 4,316,463 A * | 2/1982 | Schmitz et al. | 604/135 |
| 4,774,772 A | 10/1988 | Vetter et al. | |
| 4,874,381 A | 10/1989 | Vetter | |
| 4,940,460 A * | 7/1990 | Casey et al. | 604/143 |
| 5,069,670 A | 12/1991 | Vetter et al. | |
| 5,080,649 A | 1/1992 | Vetter | |
| 5,137,528 A | 8/1992 | Crose | |
| 5,139,490 A | 8/1992 | Vetter et al. | |
| 5,185,985 A | 2/1993 | Vetter et al. | |
| 5,290,228 A | 3/1994 | Uemura et al. | |
| 5,320,603 A | 6/1994 | Vetter et al. | |
| RE34,845 E | 1/1995 | Vetter et al. | |
| 5,554,134 A * | 9/1996 | Bonnichsen | 604/240 |
| 5,785,691 A | 7/1998 | Vetter et al. | |
| 5,893,842 A * | 4/1999 | Imbert | 604/110 |
| 6,132,395 A | 10/2000 | Landau et al. | |
| 6,223,408 B1 | 5/2001 | Vetter et al. | |

(Continued)

*Primary Examiner*—Nicholas D Lucchesi
*Assistant Examiner*—Laura A Bouchelle
(74) *Attorney, Agent, or Firm*—Winston & Strawn, LLP (57) ABSTRACT

An injector with a substance container defining a substance chamber configured for containing a substance to be injected, and an injection conduit configured for injecting the substance into a patient. A driver is associated with the substance chamber for driving the substance through the injection conduit. The injector also has a channel member defining a channel that has an open configuration in which the channel fluidly communicates the substance container to the injection conduit for the injection of the substance. The channel also has a closed configuration for blocking flow of any substance in the substance container therethrough to the injection conduit for inhibiting or preventing contact with the injection conduit prior to injection.

30 Claims, 4 Drawing Sheets

U.S. PATENT DOCUMENTS

| | | |
|---|---|---|
| 6,264,629 B1 | 7/2001 | Landau |
| 6,383,168 B1 * | 5/2002 | Landau et al. ............... 604/268 |
| 6,471,669 B2 | 10/2002 | Landau |
| 6,645,170 B2 * | 11/2003 | Landau ........................ 604/68 |
| 2002/0045866 A1 | 4/2002 | Sadowski et al. |
| 2002/0183690 A1 | 12/2002 | Arnisolle |
| 2003/0083621 A1 | 5/2003 | Shaw et al. |
| 2003/0105430 A1 | 6/2003 | Lavi et al. |
| 2003/0130619 A1 | 7/2003 | Safabash et al. |

* cited by examiner

INJECTOR WITH BYPASS CHANNEL

CROSS-REFERENCE TO RELATED APPLICATIONS

This application is a continuation of PCT/US03/04382 filed Feb. 14, 2003, which claims priority of U.S. Provisional Application No. 60/357,236 filed Feb. 15, 2002, the content of which applications is expressly incorporated herein by reference thereto.

FIELD OF THE INVENTION

The invention relates to an injection device for injecting a substance into a patient. More particularly, the invention relates to an injector with a bypass channel that can be closed or opened to feed a fluid to be injected from a container to an injection conduit.

BACKGROUND OF THE PRESENT INVENTION

Injection devices are known with a cartridge that contain a medicament to be injected. The cartridges of traditional devices typically have a seal at one end that is pierced by a proximal side of a needle to open a fluid pathway from the cartridge to the needle.

For example, U.S. Pat. No. 3,375,825 discloses a prefilled syringe. A rear penetrating end of a hypodermic needle penetrates a diaphragm to expose the contents of the barrel of the syringe for injection when the needle is attached to the barrel. Similarly, U.S. Pat. No. 2,645,223 discloses a jet injection device with a cannula that has a pointed inner end that penetrates a stopper in an ampule.

U.S. Pat. No. 3,811,441 teaches an ampule with a pierceable seal. The ampule is moved against a cannula, which pierces the seal prior to injection to communicate the medicament in the ampule and the outside by way of the cannula. U.S. Pat. No. 5,137,528 describes a local-anesthetic ampule that is placed in the barrel of a hypodermic syringe. The user manually advances the ampule in the barrel towards a proximal end of the hypodermic needle of the syringe, causing this needle end to perforate a rubber diaphragm of the ampule to enable injection of the anesthetic.

Syringes are also known for mixing a liquid and a medicament that are held in different compartments. U.S. Pat. No. 4,874,381, for example, shows a hypodermic syringe with two compartments: one with a liquid phase and the other with a solid phase, which are to be mixed to form a solution prior to injection. The syringe has a first piston to displace the liquid and solution for the injection. A second piston is located between the two compartments. A bypass interconnects the two compartments when the second piston is shifted to allow the two ends of the bypass to open to opposite sides of the piston.

U.S. Pat. Nos. 6,132,395; 6,264,629; and 6,471,669 disclose needless injection apparatuses with plugs that are moved out of a cartridge when the apparatuses are assembled into a configuration that enables a subsequent injection, by an additional action by the user.

Injection devices that employ a portion of a cartridge that is pieced by a proximal side of a needle to open the cartridge typically demand high precision in manufacture and alignment of the parts to ensure that the needle pierces the cartridge properly to allow the flow of the substance through the needle. There is a need for an injection device with a sealed cartridge that can be opened reliably without requiring the puncture thereof of the cartridge to open it and which can be opened at the time the injector is fired.

SUMMARY OF THE INVENTION

The invention relates to an injector with an openable channel for releasing a flowable or fluid substance from within a container for injecting into tissue of a patient at an injection site. A preferred embodiment of the invention comprises a substance container that defines a substance chamber configured for containing a substance to be injected. An injection conduit of the injector is configured for injecting the substance into a patient. The injection conduit is a suitable conduit for making injections, including a needle or a jet nozzle that is configured for firing the substance in a fluid jet to penetrate tissue of the patient. A driver is associated with the substance chamber for driving the substance through the injection conduit. A channel member defines a channel that has open and closed configurations. In the open configuration, the channel fluidly communicates the substance container to the injection conduit for injecting the substance. In the closed configuration, the channel is configured for blocking flow of any substance in the substance container therethrough, preferably to the injection conduit to inhibit or prevent contact prior to injection between the injection conduit and substances from the container. The channel member of this embodiment is disposed in or adjacent the distal end of the container, which is disposed adjacent to the injection conduit. The channel member is preferably associated with the driver for placing the channel in the open configuration from the closed configuration upon actuation of the driver to drive the substance from the substance chamber.

In one embodiment, a blocking stopper having a closed position for blocking flow of any substance from the substance container through the channel to the injection conduit. The blocking stopper is movable to an open position for fluidly communicating the channel with the substance container for injecting the substance. Also, a firing mechanism is preferably operably associated with the driver and operable by the user to cause the driver to drive the substance sufficiently to move the blocking stopper to the open position and also to inject the substance into the patient. The firing mechanism is operable by the user to cause the driver to drive the substance sufficiently to move the blocking stopper to the open position and also to inject the substance into the patient by a single action of the user on the firing mechanism.

Preferably, the injector is assembled such that actuation of the firing mechanism to cause the substance to be injected also causes the blocking stopper to move to the open position. An energy source can be configured for driving the driver to both move the blocking stopper to the open position and inject the substance into the patient. This can allow a single action of the user to fire the injector and can keep the substance aseptically sealed within the container until practically the moment of injection, without the danger of the cartridge being opened for any significant period of time, such as if the injector is prepared and set aside for some time prior to injection. The firing mechanism comprises a trigger depressible by the user, wherein a single depression of the trigger activates the energy source for moving the blocking stopper to the open position and also to inject the substance into the patient. The injector is also preferably fully assembled and in condition for firing the trigger, and preferably all of the substance to be injected is disposed between the driver and the blocking stopper. The preferred driver comprises a plunger, and the plunger and the blocking stopper are both slideable within the container.

In one embodiment, the injector has a delivery conduit configured for delivering the substance from the container to the injection conduit, and the channel is defined in the delivery conduit and has a substance entryway that is blocked by the blocking member in the closed position and unblocked thereby in the open position. In another embodiment, the channel is defined in the blocking member, and the delivery conduit comprises a protrusion received in the channel to close the channel when the blocking member is in the closed position, and removed therefrom when the blocking member is in the open position.

The preferred embodiment has a stopper that is movable with respect to the channel between closed and open positions. The stopper has a first side facing inside the cartridge and a second side facing outside the cartridge. In the closed position, the stopper closes the channel to place the channel in the closed configuration, sealing and retaining the substance within the cartridge adjacent the first side of the stopper. Thus, the second side of the stopper of this embodiment is free from contact with the substance from the cartridge. In the open position, the stopper opens the channel to place the channel in the open configuration.

The preferred channel has a substance entryway that is blocked by the stopper in the closed position and unblocked thereby in the open position. The preferred substance container has a distal end adjacent the injection conduit, and the stopper is disposed in the distal end. The open position of the stopper is located in a first direction from the closed position and closer to the injection conduit than the closed position. Also, the preferred channel has a substance exit for delivering the substance to the injection conduit and is located in the first direction from the substance entryway. The stopper is preferably disposed in the distal end of the cartridge in the open position, and outside the cartridge in the open position.

The stopper of the preferred embodiment is longitudinally slideable with respect to the substance entryway. The channel comprises a groove along an interior surface of the channel member, with a first end of the groove comprising the entryway. The second side of the stopper has a taper configured for improving the flow of the substance around the stopper towards the injection conduit.

The driver of this embodiment comprises a plunger that is slideably received in the substance container and configured biasing the substance against the stopper to slide the stopper between the open and closed positions. The plunger is also configured for forcing the substance through the channel and through the injection conduit. A shoulder of the substance container preferably stops movement of the driver towards the blocking stopper prior to contacting the blocking stopper.

The injection conduit can have a needle with an upstream opening for receiving the substance during injection thereof. The stopper in this embodiment is preferably configured to move to the open position without the needle piercing the stopper. The second side of the stopper is preferably configured for receiving the needle when the stopper is in the open position. The stopper itself defines an internal groove configured and dimensioned to allow the substance to flow therethrough to the upstream opening of the needle when the stopper is in the open position.

The preferred channel member comprises a guide protruding towards the interior of the channel member for guiding and positioning the stopper in the open position. The preferred channel member also comprises a narrowed portion that is preferably curved inward with respect to the container and is configured for blocking movement of the stopper past the open position.

To attach the cartridge with respect to the injection conduit, the preferred embodiment includes a resilient cartridge-gripping portion engaged with the cartridge that retains the cartridge sealed and in fluid communication with the injection conduit during injection. A locking portion is in contact with the cartridge gripping portion to retain the cartridge-gripping portion in the engagement with the cartridge to withstand pressures within the cartridge during injection, which typically are in the range of about between 50 psi and 3000 psi. The cartridge preferably comprises a first end that defines a locking recess, with the cartridge-gripping portion having a plurality of resilient fingers that are received in the locking recess, and the locking portion being disposed around the fingers for retaining the fingers engaged in the locking recess.

The present invention provides an injector with a cartridge that can be kept sealed such as until the moment of the injection and that can be reliably unsealed for injecting the substance contained therein.

DETAILED DESCRIPTION OF THE PREFERRED EMBODIMENTS

Figure 1:
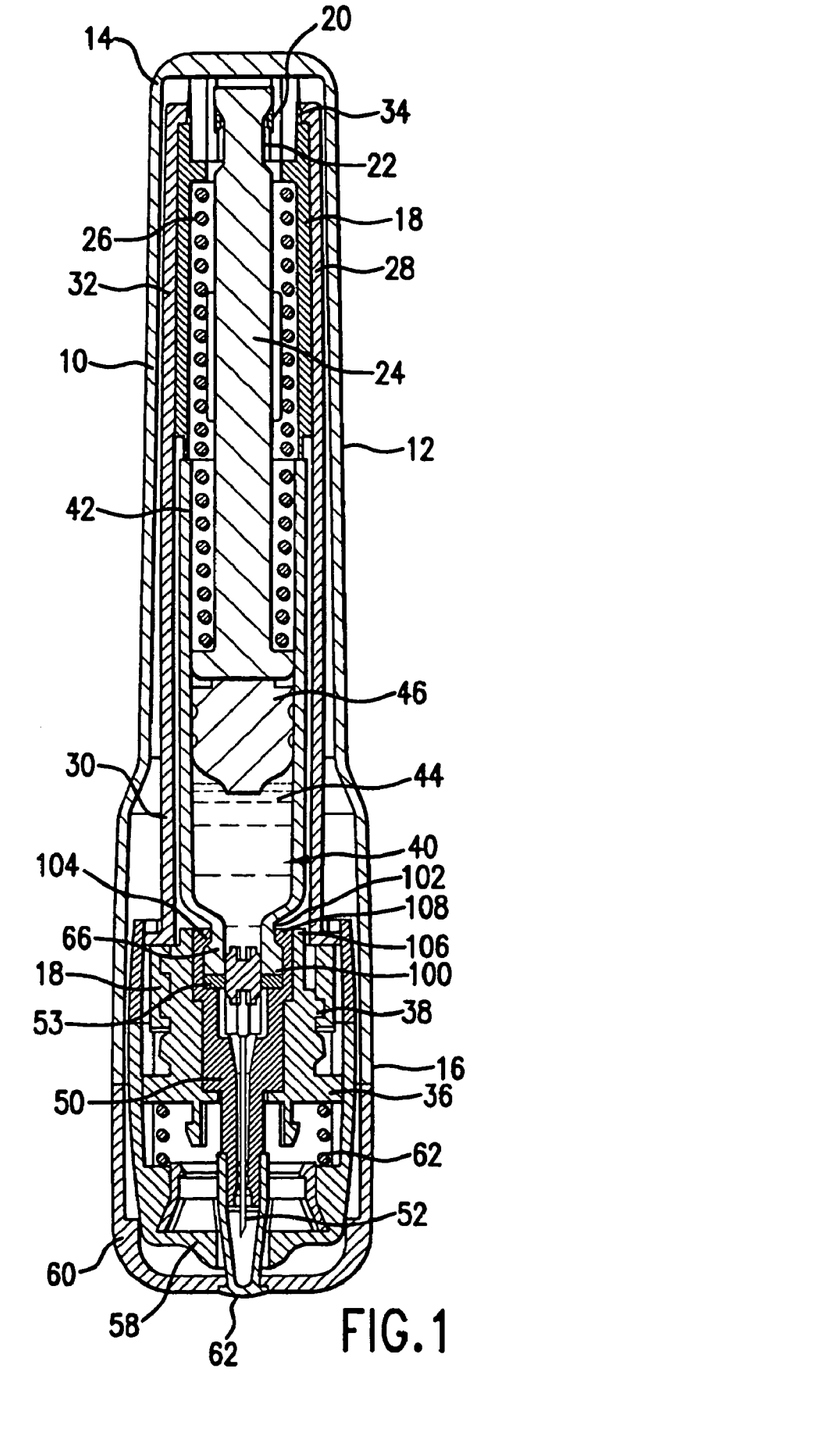
FIG. 1 is a cross-sectional view of a preferred embodiment of an injector constructed according to the present invention.

In the embodiment shown in FIG. 1, a preferred injector is shown fully assembled and ready for firing. The outer housing 10 includes a preferably elongated and cylindrical body 12 with proximal and distal end portions 14, 16. As used with respect to the embodiments in this application, the term "distal" designates the end or direction toward the front of injector towards where the injection is made, and the term "proximal" designates the end or direction toward the rear of the injector.

In the preferred embodiment, inner housing 18 is attached to the outer housing, preferably with snaps, an adhesive, a weld, or other attachment known in the art. Trigger protrusions 20 extend preferably inwardly from the proximal end of the inner housing 18 and are resiliently biased outwardly. The trigger protrusions 20 are shaped to mate with an annular recess 22 in ram 24. Ram 24 is urged toward the distal end of the injector by compression spring 26, but other energy sources capable of producing an injection, most preferably of up to about 2 mL in about 2.5 seconds or less, could be used. Examples of energizing sources are rubber elastomers and compressed gas cartridges. Another embodiment is finger actuated so that a user can press directly against a driver to operatively move the plunger. A latch 28 is slideable inside the outer housing 10 with respect to the inner housing 18, and preferably surrounds the inner housing 18. The preferred latch 28 has a barrel portion 32 at its distal side and extensions 30 at its proximal side. When the jet injector is ready to be fired, ridge 34 on the latch 28 is in contact with the trigger protrusions 20 and biases them inwardly to maintain them received in the recess 22, preventing the ram 24 from firing under the force of the compression spring 26.

A cartridge mount 36 is mounted preferably to the inner housing 18 with threads 38 or other suitable attachment and holds a cartridge assembly 40 inside the inner housing 18. In the fully assembled condition, the threads are fully threaded, and the threaded portions are configured such that further threading past the assembled position prevented. With the threads fully engaged, and the injector ready to be fired upon the activation of the triggering mechanism, such as by depressing the needle guard 58 to fire the device to inject the medicament as described below, the stopper 70 in a position closing off preferably all substance to be injected from the channels 74, also described below. From this fully assembled and fire-ready configuration, the activation of the triggering mechanism not only causes the stopper 70 to move to open the channel communicate the substance with the needle 68, but also to inject the substance, preferably without requiring any other action from the user.

Figure 2:
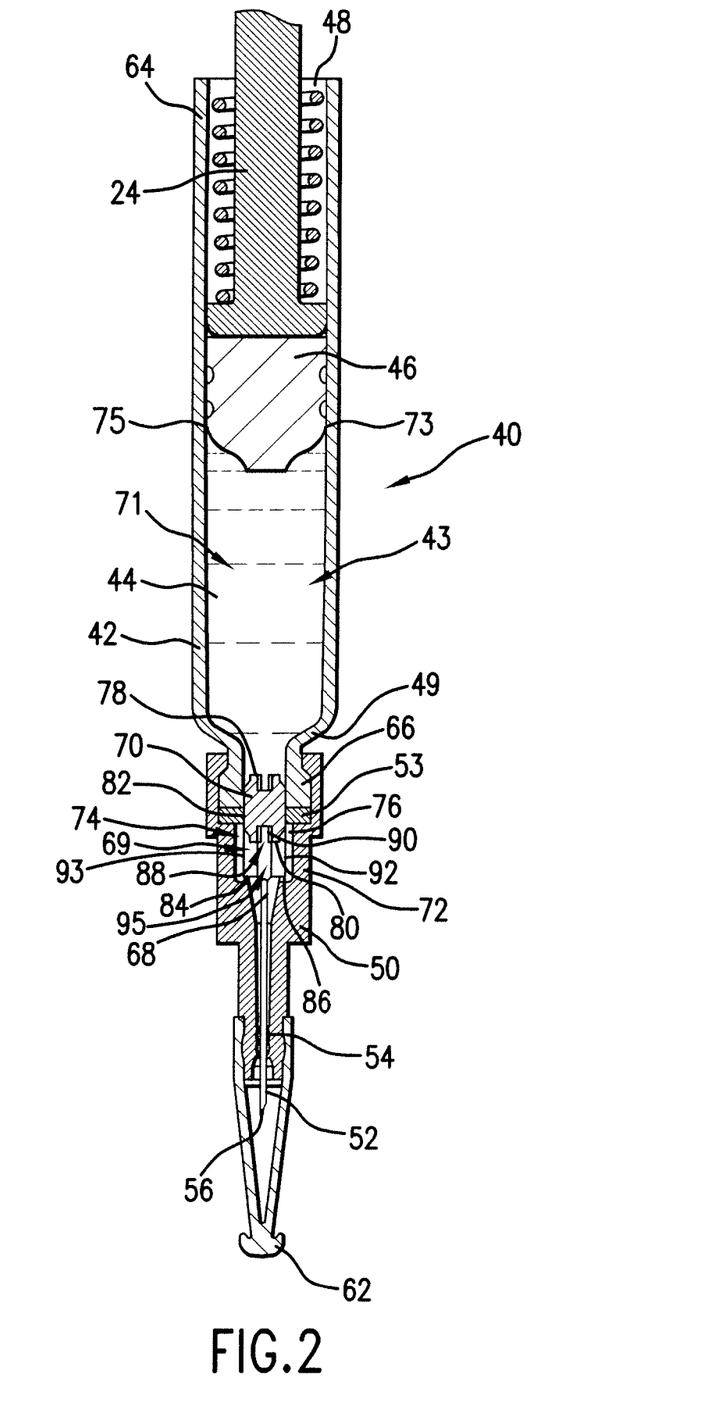
FIG. 2 is a cross-sectional view of the cartridge and injection assembly thereof in a closed configuration.
Figure 3:
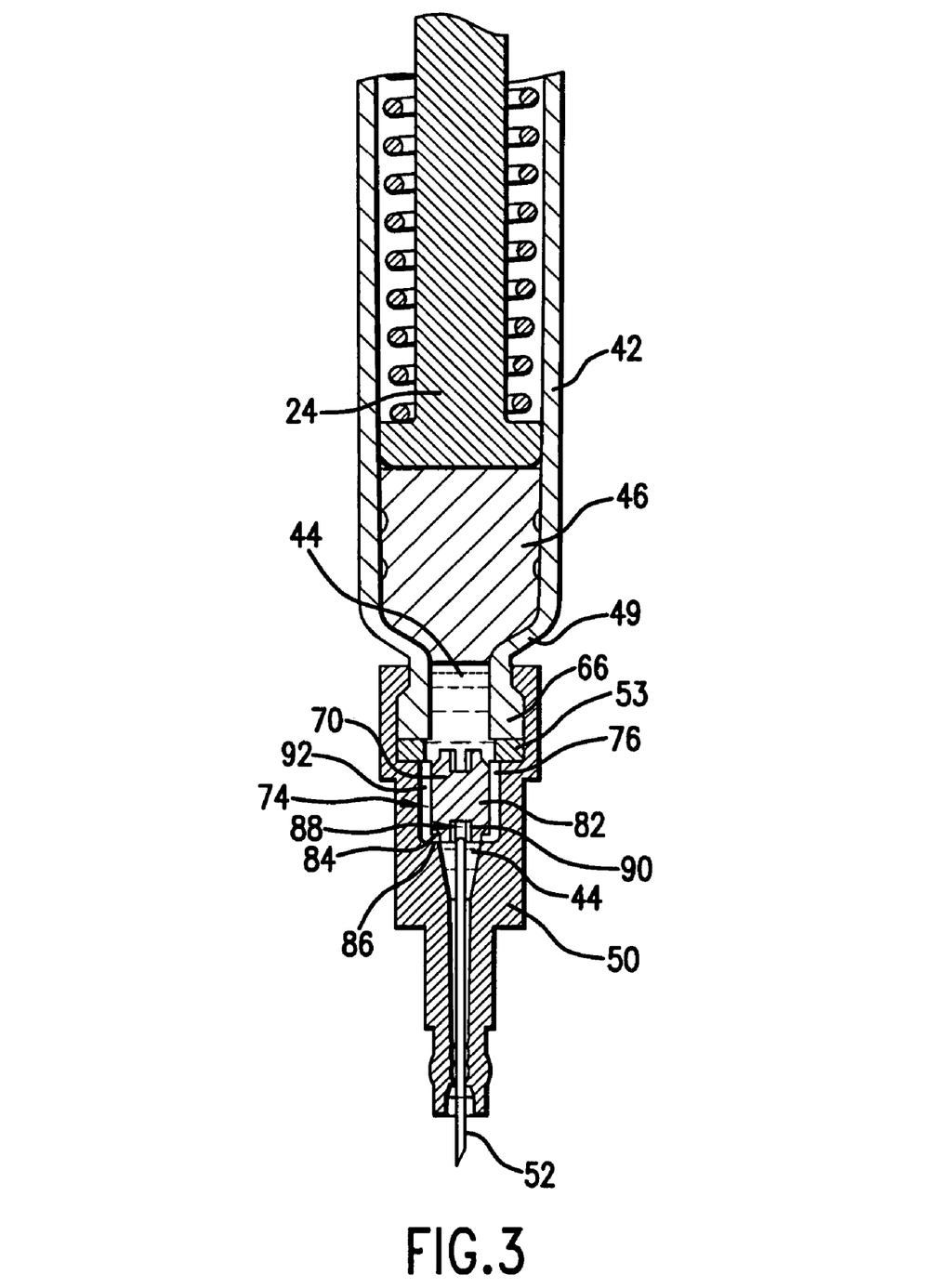
FIG. 3 is a cross-sectional view of the cartridge and injection assembly thereof in an open configuration.

Referring to FIGS. 1 and 2, cartridge assembly 40 includes a cartridge 42, which may comprise an ampule made of glass, metal, plastic, or other suitable material, typically holding about between 0.02 and 2 mL of a substance in substance chamber 43. Preferably the cartridge 42 contains one or more doses of a medicament 42. The substance is preferably a fluid medicament 44. A plunger 46, preferably made of rubber or another elastomeric material, is slideable within the cartridge 42 and associated therewith for sealing opening 48 in the proximal end of the cartridge 42 to keep the medicament 44 from leaking out. The plunger material has sufficient hardness to not adhere to the cartridge wall although it may be slightly compressible so long as it can transfer the force applied thereto to a movement that urges the medicament toward opening 48. The ram 24 extends into the opening 48 and abuts the plunger 46. A shoulder 49 is preferably provided at a narrowing portion of the cartridge 42, which is narrower than the plunger 46 to stop distal movement of the plunger 46, preferably to prevent the stopper 46 from contacting the stopper 70, as described below and as shown in FIG. 3.

The cartridge mount 36 is connected to hub 50, which preferably supports an injection conduit. In the embodiment shown, the injection conduit comprises injecting needle 52, which is attached to the hub 50, preferably by an adhesive. Preferably, grooves or a surface treatment on longitudinal pocket 54 and/or on the injecting needle 52 enhance bonding between the injecting needle 52 and the hub 50. Other methods of fixing, such as molding, may be used to secure the injecting needle 52 to the needle hub 50. Alternative embodiments of the channel include channels that are defined through the channel member, such as the hub, and that do not have an open side as do the grooves shown.

Other embodiments have different types of injection conduits. A jet injector embodiment of the invention has a jet nozzle, and the energy source and nozzle are configured for producing a jet of the substance with sufficient speed to penetrate the injection site of the patient.

The gauge of the needle 52 is selected to allow for an appropriate injection time, and in one embodiment, the needle 52 is of 27 gauge. The needle 52 has a sharp end 56 that extends beyond the distal end of the hub 50 by an amount depending on the depth of injection desired. Preferably, needle sharp end 56 extends about between 0.5 and 10 mm beyond the hub 50, and sufficiently to enter an injection site of the patient upon injection.

As shown in FIG. 1, a needle guard 58 is located at the distal end of the injecting device and preferably extends distally beyond the needle 52, preferably concealing the needle 52. The needle guard 58 is preferably slideably mounted to the housings 10,18 for sliding in a longitudinal direction with respect to the needle 52. A return spring 62 biases the needle guard 58 distally with respect to the needle 52 to the guarding position shown, such that the needle 52 is retracted within the guard 58.

The preferred embodiment features a removable safety cap 60 removably mounted over and covering the needle guard 58 to prevent its unintentional depression. The safety cap 60 includes a needle cap 62 connected thereto. The needle cap 62 forms a sterile barrier around the needle 52.

Cartridge 42 has a proximal end 64 and a distal end 66, which is preferably disposed near the proximal end 68 of the needle 52. The proximal end 68 of the needle is preferably blunt as, in the preferred embodiment, it does not need to pierce the stopper. The distal end of the cartridge 42 is received in the hub 50, and a seal such as o-ring 53 preferably seals the space between the cartridge 42 and the hub 50.

A stopper 70 is associated with the cartridge 42 to seal the medicament 44 in the substance chamber thereof. Stopper 70 is movable preferably along a longitudinal direction, distally toward the needle 52. The stopper is preferably not connected to the plunger 46 or ram 24, except via the medicament 44. In an alternative embodiment, however, a mechanical connection can join the plunger 46 or ram 24 for moving the stopper 70. In this embodiment, the medicament surrounds the mechanical connection, which may be a rod, and which is constructed of a material that is chemically resistant or inert to the medicament that contacts it. This arrangement is particularly useful when the medicament is compressible and is in a contracted state. Then, movement of the stopper to the channel open position, where the medicament can expand and flow through the needle.

The stopper 70 is preferably disposed in the distal end 66 of the cartridge 42, preferably within about 40% of the length from the proximal end of the substance containing portion 71 of cartridge 42, which includes any chambers that contain any substances to be injected, to the distal tip of the distal end 66 of the cartridge 42, more preferably within about 20% thereof, and most preferably within about 10% thereof. Measured from the distal edge 73 of sealing surface 75 of the plunger 46, which sealingly contacts the inner surface of the cartridge 42, to the distal tip of the distal end 66 of the cartridge 42, the stopper 70 is preferably disposed within about the distal 40% of this distance, more preferably within about 20% thereof, and most preferably within about 10% thereof. The stopper 70 is preferably disposed distally from the substance containing portion 71 and of all substance chambers thereof. Thus, preferably no substance from the substance containing portion is disposed between the stopper 70 and the injection conduit when the device is in the initial closed-channel state shown in FIGS. 1 and 2.

Hub 50 defines a delivery conduit 69 configured for delivering the substance from the container to the injection conduit and fluidly communicated therebetween when stopper 70 is in an open position. A channel member 72, which is preferably part of the hub 50, has a channel region that defines at least one channel 74, preferably comprising one or more internal grooves in the interior of the hub 50. Preferably, the channel 74 has a plurality of grooves. In FIG. 2, the channel 74 is in a closed configuration, with the stopper 70 in a closed position for blocking flow of any medicament 44 in the cartridge 42 therethrough to the needle 52, such that the needle 52 is substantially free from contact with any substance from the substance container to be injected prior to the injection.

In the closed position, the stopper 70 is disposed to block entryway 76 of the channel 74 from fluid communication with the cartridge chamber. In this position, the stopper 70 is preferably disposed proximally from the entryway. The medicament 44 or other substance to be injected is sealed and retained in the cartridge 42 by the stopper 70. In the closed position, a proximal face 78 of the stopper 70 faces and is in contact with the medicament 44 in the interior of the cartridge 42. In the closed position, distal face 80 of the stopper 70 is preferably free from contact with any of the medicament 44 or other substance to by injected from the cartridge 42.

The stopper 70 is preferably slideable longitudinally and distally to an open position closer to the needle 52 than in the closed position, as shown in FIG. 3, to place the channel 74 in an open configuration. In the open position, the stopper 70 unblocks and opens the channel 74 to fluidly communicate the container 42 with the needle 52 to allow the medicament 44 to be injected through the needle. In this position, the stopper 70 has preferably exited the cartridge 42 and is disposed within the hub 50.

A ledge 84 of the hub 50 projects into the interior thereof to block the stopper 70 from moving further in a distal direction than the open position. The stopper 70 preferably has a cartridge sealing portion 82, which in the embodiment shown comprises a wall in sealing association with the inside of the cartridge 42. The longitudinal length of the sealing portion 82 is preferably shorter than the longitudinal length of the channel 74, such that upon reaching the open position, the sealing portion lies between the entryway 76 and outlet 86 of the channel 74, allowing the contents of the cartridge 42 to enter the entryway 76 and flow through the channel 74 and out through the outlet 86 to the needle 52.

The grooves of the channel member 72 are preferably spaced between guide portions 92 configured and dimensioned to guide the stopper 70. The guide portions 92 provide a narrower diameter than the channel 74, and preferably maintain about the same diameter and shape as the interior of the distal end 66 of the cartridge to allow the stopper 70 to slide smoothly therein. The guide portions 92 have interior surfaces 93 that define internal passageway 95 in which the blocking stopper 70 is receivable, with the proximal and distal ends of the channels 74 extending radially exterior therefrom.

The stopper 70 is preferably tapered on one or both of its proximal and distal sides 78,80 to improve the flow of the medicament 44 around the stopper 70. A cylindrical portion 77 for sealing and sliding against the cartridge is preferably disposed between the tapered sides 78,80. Additionally, preferably the distal side 80 has a needle receiving recess 88 aligned with the proximal end 68 of the needle 52 for non-piercingly receiving the needle 52, such that in the open position, the needle 52 does not pierce the stopper 70. The proximal end of the needle is preferably blunt. The preferred distal side 80 of the stopper 70 also has channels 90 for facilitating the flow of the medicament 44 around the needle 52 when this is received in the recess 88. In the embodiment shown, both proximal and distal sides 78,80 of the stopper 70 are substantially symmetrical for ease of manufacturing, but these sides are different from each other in another embodiment.

The needle guard 58 is operatively associated with latch 28, such that pressing the needle guard 58 toward the proximal end of the device, such as upon pressing the distal end against a patient for injecting the medicament 44, causes the needle guard 58 to push the latch 28 longitudinally toward the proximal end of the device. The ridge 34 of the latch 28 thus moves off the trigger protrusions 20 on the inner housing 18. This allows the trigger protrusions 20 to flex out of the annular recess 22 in the ram 24, thereby causing the ram 24 to fire under the bias of compression spring 26. When the ram 24 fires, it slides plunger 46 in the cartridge 42 distally, causing the medicament 44 to displace the stopper 70 from the closed to the open position. With the stopper 70 in the open position, the plunger forces the medicament 44 to flow through the channel 74 around the stopper 70 and out through the needle 52 to be injected into the injection site in the patient.

Referring to FIG. 1, the distal end 66 of the cartridge 42 is preferably enlarged and is laterally to form an enlarged diameter portion 100 and an adjacent recess 102. A cartridge-gripping member 104, preferably of the hub 50, comprises a laterally or radially resilient portion 104, which in the preferred embodiment comprises a plurality of fingers, for example four fingers that extend distally around the outside of the distal end 66 of the cartridge 42. The fingers has tips 108 that extend radially inwards toward the cartridge 42 and are received in the recess 102 of the cartridge 42 and are engaged therewith to firmly attach the cartridge to the hub 50. Cartridge mount 36 preferably has a finger-locking portion 106, preferably including a ring disposed around the outside of the fingers of the gripping member 104 to retain the fingers in engagement within the recess 102, which thus functions as a locking recess, to prevent the fingers from spreading to release the cartridge or break the seal with the O-ring 53. During assembly, the distal end 66 of the cartridge is placed into the cartridge-gripping member 104, and this is placed into the finger-locking portion 106 to positively hold and seal the cartridge to the hub 50.

Preferably, the gripping member 104 and finger-locking portion 106 are made of a plastic or other material with sufficient stiffness and strength to withstand the pressures produced within the cartridge during injections. These injection pressures typically are in the range of about 50 psi to about 3000 psi. Embodiment with an injection conduit that comprises a needle typically employ an injection pressure of about between 50 psi and 300 psi, and embodiments in which the injection conduit comprises a needle-free jet nozzle typically employ an injection pressure of about between 1500 psi and 3000 psi.

Figure 4:
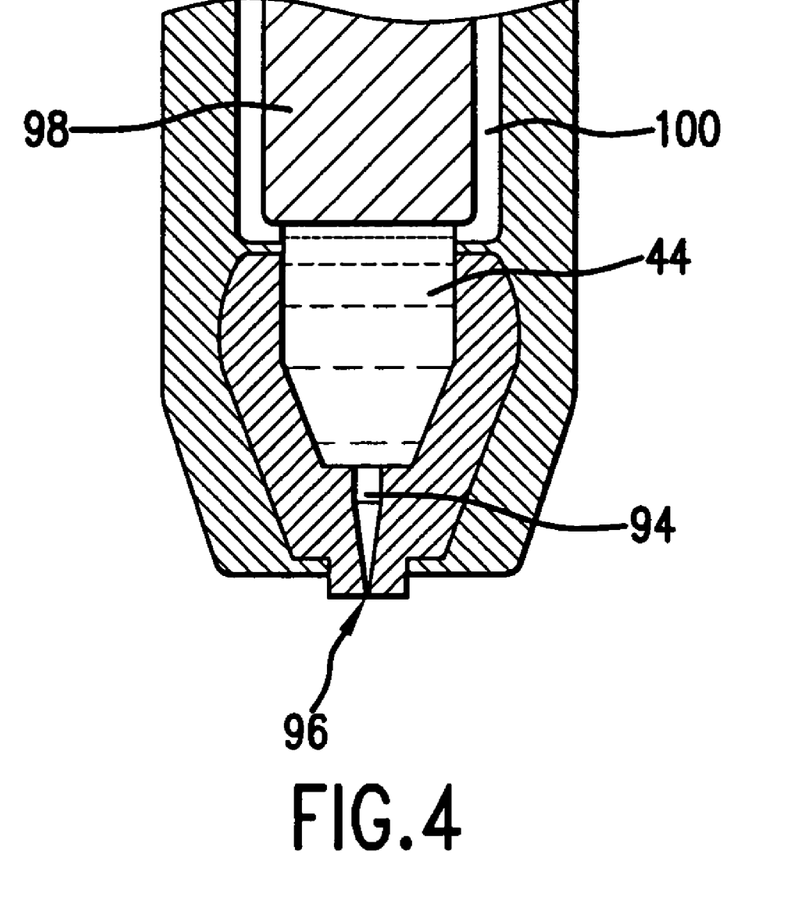
FIG. 4 is a cross-sectional view of a distal portion of another embodiment of the invention.

Referring to FIG. 4, the injection conduit of an alternative embodiment comprises a needle-free jet nozzle 94 with an orifice 96 configured and dimensioned for firing the medicament 44 in a fluid jet to penetrate tissue of the patient at the injection site. The preferred orifice is tapered in a distal direction. Stopper 98 is shown in its open position to allow the medicament 44 to flow through the fluid pathway formed by the open channel 100 to be injected out from the nozzle 94. In this embodiment, the energy source is selected to have greater force than in the embodiment of FIGS. 1-3 in order to provide sufficient pressure in the medicament 44 to produce an adequate injection jet.

In the preferred embodiments, the primary stopper, such as stoppers 70, 98 shown in FIGS. 1-4, which opens the disclosed channel is disposed at the end of the cartridge and serves to close and seal the end of the cartridge from the injection conduit to prevent any of its contents from leaking out of the cartridge. The primary cartridge preferably seals the cartridge contents prior to loading the cartridge in the injection device. Some cartridge embodiments can have a second stopper between the plunger and the primary stopper and can be provided with a channel or an enlarged diameter portion to permit two or more flowable substances to be separated by at least the second stopper into two or more substance chambers, but to mix with each other upon injection. Preferably, there is no additional stopper between the primary stopper and the injection conduit.

Figure 5:
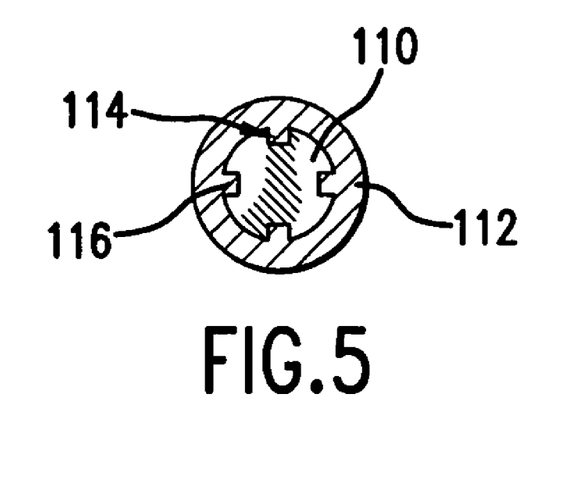
FIG. 5 is a cross-sectional end view through a neck of a substance container of another embodiment of an inventive injector, showing a stopper in a closed position.

Referring to FIG. 5, the embodiment shown has the channels 114 defined within stopper 110, which is thus the channel member. This is opposed to the embodiments of FIGS. 1-4, in which the channel member defining the channels is the needle hub. Ribs 116 of the substance container 112 extend inwardly and are sealingly receive in the channels 114 with the stopper 110 in the closed position to block the flow of the substance out of the container. The stopper 110 slides axially, when the substance in the container is displaced by the plunger during the firing of the device, past the ribs 116 to remove them from the channels 114 and allow the substance to flow through the channels 114 to be injected.

While illustrative embodiments of the invention are disclosed herein, it will be appreciated that numerous modifications and other embodiments may be devised by those skilled in the art. For example, the channel member can be constructed as part of the cartridge. Also, other embodiments have trigger mechanisms that can be actuated from different parts of the device, such as an embodiment with a depressible trigger on or near the proximal end of the device housing, for instance including a button. Additionally, when the stopper of the preferred embodiment is placed in the open position, the injector is preferably configured such that the injector cannot be used again, although other embodiments are foreseen that can be cleaned, refilled, and reused. Therefore, it will be understood that the appended claims are intended to cover all such modifications and embodiments that come within the spirit and scope of the present invention.

What is claimed is:

1. An injector, comprising:
    a substance container defining a substance chamber configured for containing a substance to be injected;
    an injection conduit configured for injecting the substance into a patient;
    a driver associated with the substance chamber for driving the substance through the injection conduit;
    a channel member having an interior surface that defines an internal passageway open to the substance chamber, the channel member defining a channel that has a first end open towards the internal passageway for receiving the substance from the chamber and a second end open towards the injection conduit, the channel extending radially exterior to a portion of the interior surface and internal passageway between the first and second ends for bypassing the internal passageway to fluidly communicate the substance container to the injection conduit from the first end to the second end for injecting the substance;
    a blocking stopper having a closed position for blocking flow of any substance from the substance container through the channel to the injection conduit, the blocking stopper being movable within the internal passageway with respect to the channel ends to an open position for unblocking the flow of the substance from the chamber to the first end, through the channel around the blocking stopper to the second end, and to the injection conduit for injecting the substance, wherein the channel member comprises a guide protruding inwardly adjacent the groove to the interior surface for defining a circumferential side of the channel and for guiding and positioning the stopper in the open position;
    a firing mechanism operably associated with the driver and operable by the user to cause the driver to drive the substance sufficiently to move the blocking stopper to the open position and also to inject the substance into the patient; and
    an energy source configured for driving the driver to both move the blocking stopper to the open position and inject the substance into the patient.

2. The injector of claim 1, wherein the firing mechanism is operable by the user to cause the driver to drive the substance sufficiently to move the blocking stopper to the open position and also to inject the substance into the patient by a single action of the user on the firing mechanism.

3. The injector of claim 1, wherein the injector is assembled such that actuation of the firing mechanism to cause the substance to be injected also causes the blocking stopper to move to the open position.

4. The injector of claim 1, wherein the injector is fully assembled and in condition for firing the substance with the blocking stopper in the closed position.

5. The injector of claim 1, wherein substantially all of the substance to be injected is disposed between the driver and the blocking stopper.

6. The injector of claim 5, wherein the driver comprises a plunger, and both the plunger and the blocking stopper are slideable within the container.

7. The injector of claim 1, wherein the substance container has a distal end disposed adjacent the injection conduit, and the channel member is disposed in or adjacent the distal end.

8. The injector of claim 1, wherein the injection conduit comprises a needle-free jet nozzle configured for firing the substance in a fluid jet sufficient to penetrate tissue of the patient.

9. The injector of claim 1, wherein the injection conduit comprises a needle, and the channel member comprises a needle hub supporting the needle and attached to the substance container.

10. The injector of claim 1, wherein the container comprises a cartridge that defines a locking recess, the injector further comprising:
    a resilient cartridge-gripping portion comprising a plurality of resilient fingers that are received in the locking recess and thereby engaged with the cartridge to retain the cartridge sealed and in fluid communication with the injection conduit during injection; and
    a locking portion disposed around the fingers to retain the cartridge-gripping portion in the engagement with the cartridge to withstand pressures within the cartridge during injection.

11. The injector of claim 1, wherein the substance container comprises a shoulder to stop movement of the driver towards the blocking stopper prior to moving into contact herewith.

12. An injector, comprising:
    a substance container defining a substance chamber configured for containing a substance to be injected;
    an injection conduit configured for injecting the substance into a patient;
    a driver associated with the substance chamber for driving the substance through the injection conduit;
    a channel member having an interior surface that defines an internal passageway open to the substance chamber, having a channel region defining a channel that has a first end open towards the internal passageway for receiving the substance from the chamber and a second end open towards the injection conduit, channel extending radially exterior to the interior surface and internal passageway at a location between the first end and second ends for bypassing the internal passageway in an open configuration to fluidly communicate the substance container to the injection conduit from the first end to the second end for injecting the substance;
    a blocking stopper having a closed position downstream of any substance to be injected that is contained in the container and being movable with respect to the channel between the closed position and an open position, in the closed position the stopper being disposed at least partially outside the channel region for blocking flow of the substance between the chamber and the first end of the channel for sealing and retaining the substance within the chamber, and in the open position the stopper being disposed within the channel region between the first and second ends for cooperating with the channel to allow the substance to flow from the chamber to the first end, through the channel around and past the blocking stopper to the second end, and to the injection conduit, wherein the channel member comprises a guide protruding inwardly adjacent the groove to the interior surface for defining a circumferential side of the channel and for guiding and positioning the stopper in the open position; and a firing mechanism operably associated with the driver and operable by the user to cause the driver to drive the substance sufficiently to move the blocking stopper to the open position and also to inject the substance into the patient.

13. The injector of claim 12, wherein the substance container has a distal end adjacent the injection conduit, and the stopper is disposed in the distal end of the container in the closed position and proximally from the first end of the channel, the open position of the stopper being disposed distally from the closed position and closer to the injection conduit than the closed position, and the second end of the channel is located distally from the first end.

14. The injector of claim 13, wherein the container comprises a cartridge that includes said distal end, and the channel member comprises a hub of separate construction than the cartridge and attached thereto, the hub including the injection conduit, the stopper being disposed in the distal end in the closed position to seal the cartridge and being disposed outside the cartridge but within the hub in the open position.

15. The injector of claim 12, wherein the channel comprises a groove in the channel member in the channel region.

16. The injector of claim 12, wherein:
the injection conduit comprises a needle having an upstream opening for receiving the substance during injection thereof; and
the blocking stopper is configured to move to the open position without the needle piercing the stopper.

17. The injector of claim 12, wherein the second side of the blocking stopper is configured for receiving the needle in the open position, the stopper defining an internal groove configured and dimensioned for allowing the substance to flow therethrough to the upstream opening of the needle in the open position.

18. The injector of claim 12, wherein the channel member comprises a narrow portion of the internal passageway that is narrower than the blocking stopper for blocking movement of the blocking stopper past the open position, wherein the second end of the channel is disposed in the narrow portion.

19. The injector of claim 12, wherein the stopper has a first side facing inside the cartridge and a second side facing the outside the cartridge, in the closed position, the stopper closing the channel for sealing and retaining the substance within the cartridge adjacent the first side of the stopper such that the second side of the stopper is free from contact with any of the substance from the cartridge.

20. The injector of claim 12, wherein the pressure within the cartridge during injection is about between 50 psi and 3000 psi.

21. The injector of claim 12, wherein the blocking stopper is movable in a longitudinal direction between the closed and open positions, and the channel extends laterally about the blocking stopper with respect to the longitudinal direction.

22. The injector of claim 9, wherein the injector is a jet injector, and the energy source and needle are configured for jet injecting the substance.

23. The injector of claim 12, wherein the channel comprises a plurality of channels, and the guide comprises a plurality of guides that are disposed between the channels for defining the channels and retaining the blocking stopper within the internal passageway.

24. The injector of claim 23, wherein the guides and channels are disposed circumferentially about the blocking stopper in the open position, such that the interior surface on the guides define the internal passageway of smaller width than a larger width measured to an outwardly disposed walls of the channels, wherein the blocking stopper has a width selected to be received within the internal passageway but narrower than said larger width so that the channels extend radially around the blocking stopper in the open position in channel region.

25. The injector of claim 12, wherein the injector is a jet injector which further comprises an energy source configured for driving the driver to both move the blocking stopper to the open position and inject the substance into the patient, and wherein the firing mechanism is operably associated with the energy source and operable by the user to cause the energy source to drive the driver for driving the substance sufficiently to move the blocking stopper to the open position and also to jet inject the substance into the patient.

26. The injector of claim 25, wherein the firing mechanism comprises a trigger mechanism activatable by the user, wherein a single activation of the trigger activates the energy source for moving the blocking stopper to the open position and also to inject the substance into the patient.

27. The injector of claim 25, wherein the injector is configured to prevent access to the driver for preventing refilling of the injector once the energy source is operated to inject the substance.

28. The injector of claim 12, wherein the blocking stopper has a blocking portion that seals the chamber in the closed position, the blocking portion having a longitudinal length that is shorter than a length of the channel between the first and second ends to enable the channel allow the substance to flow around and radially exterior to the blocking stopper in the open position.

29. The injector of claim 12, wherein the second end is open to the internal passageway.

30. The injector of claim 15, wherein the groove is open to the internal passageway along its length.

* * * * *